US00PP18936P2

(12) United States Plant Patent

Serimian et al.

(10) Patent No.: US PP18,936 P2
(45) Date of Patent: Jun. 17, 2008

(54) NECTARINE TREE DENOMINATED 'AUGUST LION III'

(50) Latin Name: ***Prunus persica* var. *nectarine***
Varietal Denomination: August Lion III

(76) Inventors: Donald M. Serimian, 10463 S. Del Rey Ave., Selma, CA (US) 93662; Lionel M. Serimian, 10463 S. Del Rey Ave., Selma, CA (US) 93662

( * ) Notice: Subject to any disclaimer, the term of this patent is extended or adjusted under 35 U.S.C. 154(b) by 11 days.

(21) Appl. No.: 11/592,441

(22) Filed: Nov. 3, 2006

(51) Int. Cl.
*A01H 5/00* (2006.01)

(52) U.S. Cl. ..... Plt./190
(58) Field of Classification Search ..... Plt./190
See application file for complete search history.

(56) References Cited

U.S. PATENT DOCUMENTS

PP6,544 P * 1/1989 Serimian et al. ..... Plt./192
PP9,053 P * 2/1995 Serimian et al. ..... Plt./190

* cited by examiner

*Primary Examiner*—Wendy C. Haas
(74) *Attorney, Agent, or Firm*—Worrel & Worrel

(57) ABSTRACT

A new and distinct variety of nectarine tree which is somewhat similar to the 'August Lion II' nectarine tree (U.S. Plant Pat. No. 9,053) but from which it is distinguished by producing fruit which are mature for harvesting and shipment approximately five (5) to seven (7) days after 'August Lion II' nectarine tree (U.S. Plant Pat. No. 9,053) in the San Joaquin Valley of central California and wherein the fruit is of high quality, has a good flavor with dark red coloration over the skin surface.

1 Drawing Sheet

Latin name of the genus and species of the plant claimed: *Prunus persica* var. *nectarine.*

BACKGROUND OF THE NEW VARIETY

The present invention relates to a new variety of nectarine tree, *Prunus persica* var *nectarina,* which will hereinafter be denominated varietally as the 'August Lion III' nectarine tree, and, more particularly, to a nectarine tree which produces very large clingstone fruit which, in a normal year, is mature for commercial harvesting and shipment approximately August 15$^{th}$ through August 30$^{th}$, or approximately five (5) to seven (7) days after 'August Lion II' nectarine tree (U.S. Plant Pat. No. 9,053), in the San Joaquin Valley of central California, having a fully red outer coloration and a distinctive flavor when ripe.

New varieties of plant life, including, of course, nectarine trees, which result from the process of hybridization require an arduous and time consuming period of selection and development. Among the objectives in selecting a new plant variety are those which appear to possess the characteristics which may prove to be a commercial success. These characteristics for the fruit thereof, include but are not limited to, size, flavor, outer coloration, resistance to disease, the capability for storage, shipment, and retail display and consumption for a commercially acceptable period of time. For the trees themselves, such considerations include growth, productivity, ease of harvesting, resistance to disease and pests and toleration of variations in climatic conditions. The instant new variety of nectarine tree is believed by the inventors to have excellent characteristics in these regards and thus is a promising candidate for commercial success.

In addition the subject variety of nectarine tree ripens for harvest later in the growing season than many varieties of nectarine tree including the 'August Lion II' nectarine tree (U.S. Plant Pat. No. 9,053). It therefore, in effect, extends the productive season for nectarine fruit produced in the San Joaquin Valley of central California, as well as in other growing areas.

ORIGIN AND ASEXUAL REPRODUCTION OF THE NEW VARIETY

The present variety of nectarine tree was discovered by the inventors in their orchard which is located near Selma in the San Joaquin Valley of central California. The inventors discovered the newly found seedling in the spring of 2001. The seedling was the result of cross pollination between the 'Summer Lion II' nectarine tree (U.S. Plant Pat. No. 6,544) and the 'August Lion II' nectarine tree (U.S. Plant Pat. No. 9,053). In the spring of 2001, budwood was selected by the inventors from the new variety of nectarine tree and was grafted on to Nemaguard rootstock planted in the same orchard. The inventors have observed the asexually reproduced trees and found that, in all respects, the resulting progeny are identical to that of the original tree of the new variety.

SUMMARY OF THE NEW VARIETY

The nectarine tree of the new variety is characterized by producing a fruit which is ripe for commercial harvesting and shipment August 15$^{th}$ through August 30$^{th}$ in a normal growing season in the San Joaquin Valley of central California. This is about five (5) to seven (7) days later than the 'August Lion II' nectarine tree (U.S. Plant Pat. No. 9,053). The fruit of the new variety of the present invention is similar in appearance to that of the 'August Lion II' nectarine tree (U.S. Plant Pat. No. 9,053) but, when mature, are more intensely colored in an almost completely red skin coloration and the fruit is slightly larger. Having a ripening date which is almost a week later than the 'August Lion II' nectarine tree (U.S. Plant Pat. No. 9,053) makes this new variety valuable in extending the commercial season for the fruit thereof.

BRIEF DESCRIPTION OF THE DRAWING

The drawing is a color photograph of portions of the instant new variety of nectarine tree displaying at the upper portion of the photograph foliage thereof; in the central portion of the photograph fruit of the new variety sectioned to expose the flesh thereof with the stone left in place; therebelow, a stone thereof; and in the lower portion of the photograph on the left a side elevation and view of a whole fruit showing the suture, centrally a top plan view of a whole fruit showing the stem end thereof and on the right a bottom plan view showing the apex thereof.

DETAILED DESCRIPTION

Referring more specifically to the botanical details of this new and distinct variety of nectarine tree, the following has been observed under the ecological conditions prevailing at the orchard of origin near Selma in the San Joaquin Valley of central California, in the United States of America. All major color code designations are by reference to the *Dictionary of Color,* by Maerz and Paul, First Edition, 1930. Common color names are also occasionally employed.

TREE

Generally:

*Size.*—Medium, 365.76 cm (12 feet) to 426.72 cm (14 feet) high with a spreading width of 304.8 cm (10 feet) to 396.24 cm (13 feet).

*Vigor.*—Very good with approximately 30.48 cm (1 foot) to 45.72 cm (1.5 feet) of annual new growth.

*Chilling requirements.*—Normal for nectarine trees in the San Joaquin Valley of central California.

*Figure.*—Upright and spreading.

*Productivity.*—Very good to excellent with large, firm fruit.

*Regularity of bearing.*—Regular.

Trunk:

*Size.*—77.47 cm (30.5 inches) in circumference, 20.32 cm (8 inches) above the ground.

*Surface texture.*—Rough.

*Color.*—Pl.8 J8 Java Brown.

*Lenticels.*—Numbers — Many on trunk surface. Size — Length — 0.3 cm (0.12 inch). Width — 0.1 cm (0.04 inch).

Branches:

*Size.*—38.1 cm (15 inches) in circumference, 43.18 cm (17 inches) above crotch, angle of scaffold branches approximately 42°.

*Surface texture.*—Mature — Nearly smooth. Immature — Smooth.

*Color.*—Mature branches — Pl.7 E10 Chestnut, Brownstone +. Immature branches — Pl.18 L8 Eve gr.

*Lenticels.*—Size — Small, 0.1 cm (0.04 inch) to 0.2 cm (0.079 inch) long. Number — Many.

Leaves

*Size.*—Length — 16.51 cm (6.5 inches) to 18.49 cm (7.28 inches). Width — 3.81 cm (1.5 inches) to 5.21 cm (2.05 inches).

*Shape.*—Lanceolate.

*Color.*—Upwardly disposed surface — Pl.23 J8 Mt. Vernon Green. Downwardly disposed surface — Pl.21 L8 shade of light green.

*Marginal form.*—Crenate.

*Veins.*—Pinnately veined. Mid Vein — Thickness — 0.1 cm (0.04 inch). Color — Pl.17 I6 Viridine green.

*Leaf margin.*—Slightly undulate.

*Glandular characteristics.*—Shape — Reniform — 2 on each side of leaf at base. Color — Pl.18 L6 Love Bird.

*Petiole.*—Size — Length — 0.89 cm (0.35 inch) to 1.5 cm (0.59 inch). Thickness — 0.15 cm (0.06 inch) to 0.2 cm (0.079 inch). Color — Pl.17 I6 Viridine green.

*Stipules.*—Number — 1. Size — 0.2 cm (0.079 inch) by 0.2 cm (0.079 inch) on mature branches, doubled on growing terminal. Color — Pl.8 Brazil.

FLOWERS

*Flower buds.*—Shape — Conic. Size — Length — 0.89 cm (0.35 inch). Width — 0.71 cm (0.28 inch) to 0.79 cm (0.31 inch).

*Calyx.*—5 with some pubescence on the sides. Color — Pl.55 L12 Vineyard Oporoto +.

*Flowers.*—Date of Bloom — Mar. 6, 2006, 40% to 50%. Size — Large when fully opened. Diameter — 5 cm (1.97 inch) to 5.21 cm (2.05 inch).

*Bloom quantity.*—Essentially on new growth — one to two blooms in cluster.

*Petals.*—Number — 5. Size — Generally large. Length — 2.21 cm (0.87 inch) to 2.31 cm (0.91 inch). Width — 1.7 cm (0.67 inch) to 2.11 cm (0.83 inch). Form — Broadly ovate with undulated margins. Color — From Pl.6 B1 light pink to Pl.1 G3 danger pink. At base Pl.3 G4.

*Claws.*—Size — Small, 2.01 cm (0.79 inch). Color — Pl.3 G4.

*Pedicel.*—Size — Short. Length — 0.1 cm (0.04 inch). Width — 0.2 cm (0.079 inch).

*Sepals.*—Number — 5. Color — Pl.55 L12 Vineyard Operto +. Size — Length — 0.71 cm (0.28 inch). Width — 0.61 cm (0.24 inch) to 0.71 cm (0.28 inch).

*Stamens.*—Number — 26 to 28. Size — Length — 1.5 cm (0.59 inch) to 1.8 cm (0.71 inch).

*Filament.*—Color — From Pl.1 C1 to Pl.1 J4 Rose Neyron.

*Anthers.*—Shape — Some-what rounded. Color — Pl. GK11 Caulderon Redwood Morocco R.

*Pistil.*—Size — 2.03 cm (0.8 inches). Color — Pl.17 Rose d'Athosa.

*Ovary.*—Color — Pl.20 L9 Piquant gr.

FRUIT

Maturity when described: Ripe for commercial harvesting and shipment approximately August 15$^{th}$ through August 30$^{th}$ in the San Joaquin Valley of central California.

*Size.*—Large. Weight — Four fruit weight 1,237.4 grams (44 oz), average 198.5 grams (7 oz). Diameters in the Axial Plane — 7.39 cm (2.91 inch) to 8 cm (3.15 inch). Transverse in the Suture Plane — 6.6 cm (2.6 inch) to 7.39 cm (2.91 inch). Transverse at Right Angles to Suture Plane — 6.6 cm (2.6 inch) to 7.39 cm (2.91 inch).

*Form.*—Uniformity — Uniform. Symmetrical or asymmetrical — Symmetrical. Suture — From apex to base — Visible and moderate. Ventral Surface — Smooth.

*Stem cavity.*—Size — Width — 1.5 cm (0.59 inch) to 1.8 cm (0.71 inch). Depth — 1.4 cm (0.55 inch) to 1.8 cm (0.71 inch). Length — 2.01 cm (0.79 inch) to 2.31 cm (0.91 inch). Shape — Ovate.

*Stem.*—Size — Short — 0.3 cm (0.12 inch) to 0.51 cm (0.2 inch). Caliper — 0.3 cm (0.12 inch) to 0.41 cm (0.16 inch).

*Apex.*—Rounded.

*Pistil point.*—Oblique.

Skin and flesh:

*Thickness.*—Normal for nectarines.

*Texture.*—Firm, glabrous.

*Tendency to crack.*—None observed.

*Color.*—Blush Color — From Pl.5 L6 Red Cross to Pl.55 H7 Gooseberry. Ground Color — Pl.10 L6 Ta Ming. Flesh Color — Pl.9 K3 Empire Y with reddish flecks and streaks to the pit cavity, Pl.4 K3 Fragonard. Color of Surface Pit Cavity — Pl.7 J6 Garnet and Spanish Lime — Pigeon Blood. Color of Pit Well — Pl.7 J6 Garnet, Spanish Lime, Pigeon Blood.

*Juice Production.*—Very good.

*Flavor.*—Very good.

*Aroma.*—Very aromatic.

*Texture.*—Firm.

*Fibers.*—Number — Few. Texture — Firm.

*Ripening.*—Evenly.

*Eating quality.*—Very good.

Stone:

*Free or clingstone.*—Clingstone.

*Fibers.*—Number — Few. Color — Pl.7 J6 Garnet. Size — 0.76 cm (0.3 inch) to 0.99 cm (0.39 inch).

*Size.*—Medium to large. Length — 3.81 cm (1.5 inch) to 4.19 cm (1.65 inch). Width — 2.9 cm (1.14 inch) to 3.2 cm (1.26 inch). Thickness — 2.31 cm (0.91 inch) to 2.49 cm (0.98 inch).

*Form.*—Ovate.

*Apex shape.*—Rounded to acute.

*Color.*—Dry — Ridges are Pl.6 J12 Port Wine, while the remainder of the stone is Pl.49 B9 Lisbon Pr.

*Base shape.*—Flat.

*Sides.*—Slanted.

*Hilum.*—Ovate.

*Ridges.*—Throughout Stone — Heavy. Dorsal Edge — More tightly grooved. Ventral Edge — Wider.

*Tendency to split.*—None observed.

Use — Fresh market.

Keeping and Shipping Quality — Very good.

Resistance To Disease — None known.

Harvesting and Shipping — August $15^{th}$ through August $30^{th}$.

Although the new and distinct variety of nectarine tree of the present invention possesses the described characteristics noted above as a result of the growing conditions prevailing near Selma in the central part of the San Joaquin Valley of California, it is to be understood that variations of the usual magnitude and characteristics incident to changes in growing conditions, irrigation, fertilization, pruning, pest control, climatic variations and the like are to be expected.

Having thus described and illustrated our new variety of nectarine tree, what we claim as new and desire to be secured by Plant Letters Patent is:

1. A new and distinct variety of nectarine tree substantially as illustrated and described which is somewhat similar to the 'August Lion II' nectarine tree (U.S. Plant Pat. No. 9,053), but from which it is distinguished by producing fruit which are mature for commercial harvesting and shipment approximately August $15^{th}$ through August $30^{th}$, or about five to seven days after the fruit of the 'August Lion II' nectarine tree (U.S. Plant Pat. No. 9,053) in the San Joaquin Valley of central California and which has a distinct, intense red coloration over its entire skin surface.

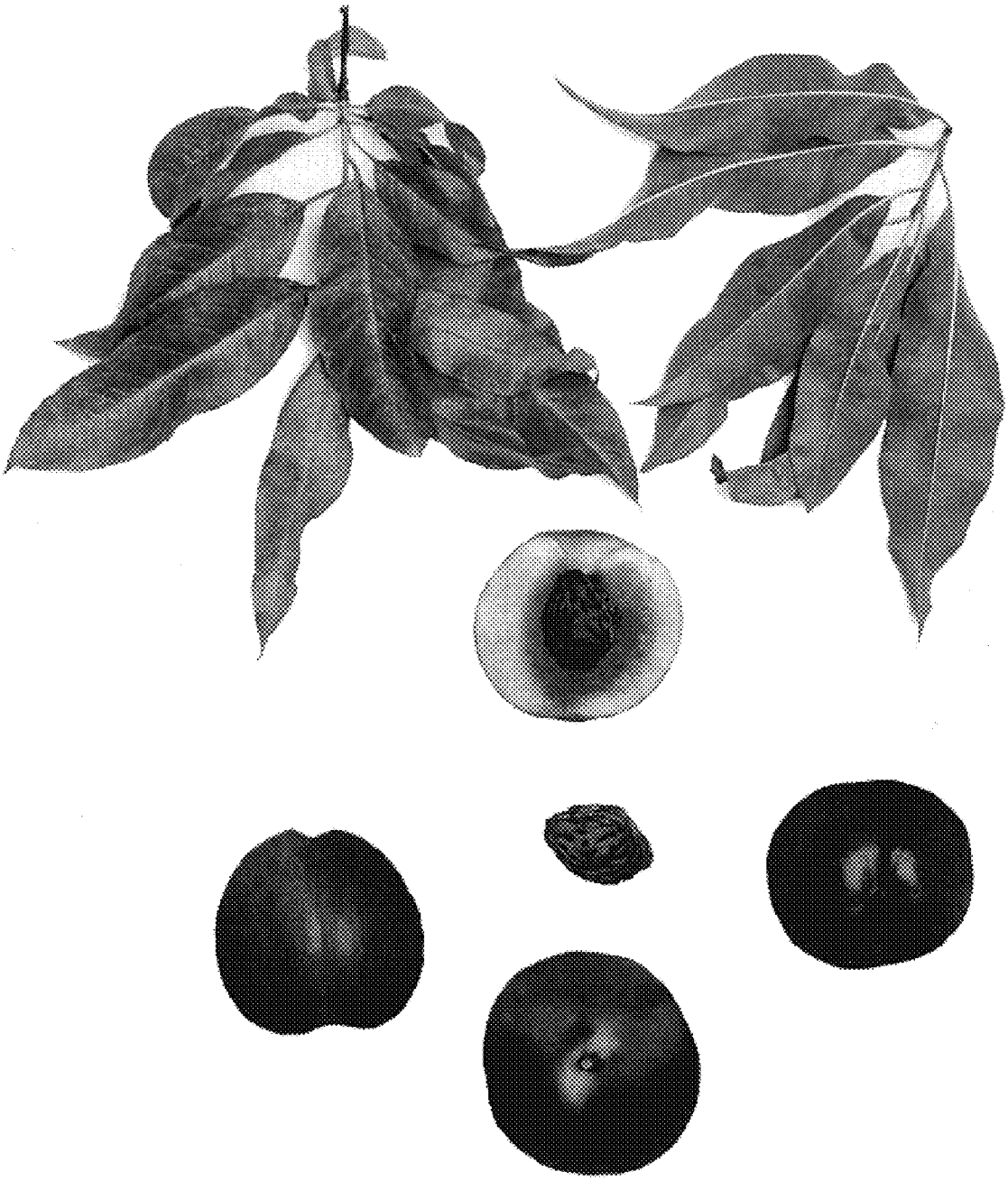

* * * * *